(12) United States Patent
Shah et al.

(10) Patent No.: US 6,830,583 B2
(45) Date of Patent: *Dec. 14, 2004

(54) THROMBORESISTANT COATING COMPOSITION

(75) Inventors: Chirag B Shah, Nashua, NH (US); Laurel L Wolfgang, Townsend, MA (US)

(73) Assignee: Medtronic Ave, Inc., Santa Rosa, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 09/862,710

(22) Filed: May 23, 2001

(65) Prior Publication Data

US 2001/0034336 A1 Oct. 25, 2001

Related U.S. Application Data

(62) Division of application No. 09/138,464, filed on Aug. 21, 1998, now Pat. No. 6,248,127.

(51) Int. Cl.[7] ............................. A61F 2/06; B32B 25/20
(52) U.S. Cl. ...................... 623/1.15; 427/2.1; 428/34.6; 428/34.7; 428/35.2; 428/35.7; 428/36.91; 428/442; 428/423.1; 428/425.6; 428/425.8; 428/447; 428/450; 428/451; 428/458; 428/463; 428/480; 428/522
(58) Field of Search .......................... 106/287.1, 287.11, 106/287.16, 124.4; 528/25, 28, 29, 26.5; 514/56, 63; 536/21; 623/1.15; 427/2.1; 428/34.6, 34.7, 35.2, 35.7, 36.91, 442, 423.1, 425.6, 425.8, 447, 450, 451, 458, 463, 480, 522; 556/413, 415, 465

(56) References Cited

U.S. PATENT DOCUMENTS

| | | | |
|---|---|---|---|
| 3,549,409 A | 12/1970 | Dyck | 117/47 |
| 3,639,141 A | 2/1972 | Dyck | 117/47 A |
| 4,082,727 A * | 4/1978 | Nagata et al. | 128/DIG. 21 |
| 4,096,239 A | 6/1978 | Katz et al. | 424/21 |
| 4,373,009 A | 2/1983 | Winn | 428/424.2 |
| 4,529,614 A | 7/1985 | Burns | 427/2 |
| 4,632,842 A | 12/1986 | Karwoski et al. | 427/2 |
| 4,678,660 A | 7/1987 | McGary et al. | 424/25 |
| 4,718,907 A | 1/1988 | Karwoski et al. | 623/12 |
| 4,720,512 A | 1/1988 | Hu et al. | 523/112 |
| 4,836,646 A | 6/1989 | Parker et al. | 350/96.34 |
| 4,844,986 A | 7/1989 | Karakelle et al. | 428/447 |
| 4,973,680 A * | 11/1990 | Billmers | 536/58 |
| 5,010,141 A | 4/1991 | Mueller | 525/276 |
| 5,013,717 A | 5/1991 | Solomon et al. | 514/56 |
| 5,026,607 A | 6/1991 | Kiezulas | 428/423.7 |
| 5,053,048 A | 10/1991 | Pinchuk | 623/1 |
| 5,077,372 A | 12/1991 | Hu et al. | 528/70 |
| 5,081,031 A | 1/1992 | Tsilibary et al. | 435/240.23 |
| 5,084,151 A | 1/1992 | Vallana et al. | 204/192.11 |
| 5,084,315 A | 1/1992 | Karimi et al. | 428/36.6 |
| 5,133,845 A | 7/1992 | Vallana et al. | 204/192.15 |
| 5,134,192 A | 7/1992 | Feijen et al. | 525/54.1 |
| 5,135,516 A | 8/1992 | Sahatjian et al. | 604/265 |
| 5,160,790 A | 11/1992 | Elton | 428/412 |
| 5,229,172 A | 7/1993 | Cahalan et al. | 427/536 |
| 5,262,451 A | 11/1993 | Winters et al. | 523/112 |
| 5,308,641 A | 5/1994 | Cahalan et al. | 427/2 |
| 5,336,518 A | 8/1994 | Narayanan et al. | 623/1 |
| 5,342,693 A | 8/1994 | Winters et al. | 428/447 |
| 5,350,800 A | 9/1994 | Verhoeven et al. | 525/54.2 |
| 5,356,433 A | 10/1994 | Rowland et al. | 623/11 |
| 5,417,969 A | 5/1995 | Hsu et al. | 424/78.27 |
| 5,441,759 A | 8/1995 | Crouther et al. | 427/2.3 |
| 5,541,167 A | 7/1996 | Hsu et al. | 514/56 |
| 5,543,019 A | 8/1996 | Lee et al. | 204/192.15 |
| 5,558,900 A | 9/1996 | Fan et al. | 427/2.28 |
| 5,576,072 A | 11/1996 | Hostettler et al. | 427/532 |
| 5,607,475 A | 3/1997 | Cahalan et al. | 623/11 |
| 5,643,580 A | 7/1997 | Subramaniam | 424/400 |
| 5,643,681 A | 7/1997 | Voorhees et al. | 428/483 |
| 5,645,931 A | 7/1997 | Fan et al. | 428/334 |
| 5,650,234 A | 7/1997 | Dolence et al. | 428/447 |
| 5,662,960 A | 9/1997 | Hostettler et al. | 427/2.3 |
| 5,672,638 A | 9/1997 | Verhoeven et al. | 523/112 |
| 5,679,659 A | 10/1997 | Verhoeven et al. | 514/56 |
| 5,702,808 A | 12/1997 | Ljungberg | 428/216 |
| 5,767,108 A | 6/1998 | Cahalan et al. | 514/56 |
| 5,804,318 A | 9/1998 | Pinchuk et al. | 428/421 |
| 5,811,151 A | 9/1998 | Hendriks et al. | 427/2.24 |
| 5,877,263 A | 3/1999 | Patnaik et al. | 525/453 |
| 5,928,279 A | 7/1999 | Shannon et al. | 623/1 |
| 5,955,588 A | 9/1999 | Tsang et al. | 536/21 |
| 5,962,138 A | 10/1999 | Kolluri et al. | 428/411.1 |
| 6,048,695 A * | 4/2000 | Bradley et al. | 435/6 |
| 6,107,416 A | 8/2000 | Patnaik et al. | 525/453 |
| 6,248,127 B1 * | 6/2001 | Shah et al. | 623/1.15 |

FOREIGN PATENT DOCUMENTS

| | | | |
|---|---|---|---|
| EP | 0 338 418 A1 | 10/1989 | |
| EP | 0 379 156 B1 | 7/1990 | |
| EP | 0 517 890 B1 | 12/1992 | |
| EP | 0 581 576 A1 * | 2/1994 | C08F/8/42 |
| EP | 0 592 870 A1 | 4/1994 | |
| WO | WO 96/24392 * | 8/1996 | A61L/27/00 |
| WO | WO 98/02197 A1 | 1/1998 | |
| WO | WO 98/08551 | 3/1998 | |

* cited by examiner

Primary Examiner—Jeffrey B. Robertson

(57) ABSTRACT

Coatings are provided in which biopolymers may be covalently linked to a substrate. Such biopolymers include those that impart thromboresistance and/or biocompatibility to the substrate, which may be a medical device. Coatings disclosed herein include those that permit coating of a medical device in a single layer, including coatings that permit applying the single layer without a primer. Suitable biopolymers include heparin complexes, and linkage may be provided by a silane having isocyanate functionality.

30 Claims, No Drawings

THROMBORESISTANT COATING COMPOSITION

CROSS-REFERENCE TO RELATED APPLICATIONS

This application claims the benefit under 35 U.S.C. § 120 as a divisional of U.S. application Ser. No. 09/138,464, filed Aug. 21, 1998, now U.S. Pat. No. 6,248,127 B1, herein incorporated by reference in its entirey.

BACKGROUND OF THE INVENTION

1. Field of the Invention

This application relates to the field of medical devices and more particularly to the field of coatings for medical devices.

2. Background Art

Arteriosclerosis is a condition that detrimentally affects many individuals. Untreated, arteriosclerosis may lead to severe consequences, including heart damage, heart attack and death. Known treatments for arteriosclerosis have had limited success. Transluminal balloon angioplasty, wherein a balloon is inserted via a catheter into the artery of the patient and expanded, thereby simultaneously expanding the partially closed artery to a more open state, is a well-known treatment for arteriosclerosis, but long-term benefits of balloon angioplasty are limited by the problems of occlusion and restenosis, which result in re-closure of the artery A variety of intravascular stents and prostheses have been developed to support diseased arteries and thereby inhibit arterial closure after angioplasty. In particular, expandable intraluminal stents have been developed in which a catheter is used to implant a stent into the artery of the patient in a minimally invasive manner.

Like other foreign bodies placed into arteries, stents can result in coagulation or thrombosis in the intravascular environment. Thrombosis can inhibit blood flow through the stent, diminishing its effectiveness, or can cause clotting, which can threaten the life of the patient. Accordingly, methods of reducing thrombotic activity have been sought to reduce the negative side effects caused by certain stents.

A number of coatings have been developed for medical devices that are intended to promote compatibility between a particular medical device and the environment in which the medical device resides. Some of these coatings, known as thromboresistant coatings, are intended to reduce the thrombosis often associated with insertion of a foreign object, such as a medical device, into the interior of the body.

Heparin, or heparinic acid, arteven, or leparan, is a glycosaminoglycan with well-known anticoaguiant activity. Heparin is biosynthesized and stored in mast cells of various animal tissues, particularly the liver, lung and gut. Heparin is known to have antithrombotic activity as a result of its ability to bind and activate antithrombin III, a plasma protein which inhibits several enzymes in the coagulation cascade. It has been hoped that heparin coatings, by inhibiting thrombogenesis, can improve the therapeutic outcomes derived from intravascular medical devices, such as stents.

However, known heparin coatings are subject to a number of defects, including incompatibility with the organism and/or microscopic features of the surface to be coated, excessive thickness, difficulty in application, and insufficient durability. For example, several known coatings are based upon simultaneous coulombic interactions between heparin and tri(dodecyl)methylammonium chloride, which is also referred to herein as heparin-TDMAC, and hydrophobic interactions between the quaternary ammonium ion of heparin-TDMAC and the surface of the device. Due to the relative weakness of hydrophobic interactions, such coatings typically leach away from the substrate to which they are applied within a few hours; coatings of this type, therefore, are not generally durable enough to provide beneficial therapeutic results.

Other known coatings comprise silanes having a pendent amino or vinyl functionality. In the fabrication of these coatings, a base layer of silane is applied initially to the surface, followed by the application to the base layer of a second layer comprising antithrombogenic biomolecules, such as heparin. It is necessary that the pendent groups of the base layer of silane be both complementary and accessible to groups on heparin. In some such coatings, a silane with terminal amino functionality is applied to a substrate to form a first layer, followed by application of heparin in solution to form the second layer. In certain examples of this strategy, the amino functionality of the silane base layer reacts with an aldehyde-containing heparin derivative to form a Schiff base and thereby covalently attach the biomiolecule to the base layer. In another group of coatings of this general class, a base layer comprising a silane with a vinyl functional group is applied to a surface, followed by covalent attachment, via free radical chemistry, of a heparin-containing derivative to the base layer.

Some of the known coatings have been found lacking in bioeffectiveness and stability. Modifications made in these coatings utilize additional coatings of polymeric matrices comprising reactive functionalities. The multi-step process required to fabricate the polymeric matrices necessary in these approaches increases the thickness of the resulting coatings. Thick coatings present a number of difficulties. First, thick coatings increase the profile of the medical device in the intravascular environment. A stent with a thick profile, for example, can reduce blood flow, thereby undermining the therapeutic benefit of the stent. A thick coating may also render the coating itself more vulnerable to pitting, chipping, cracking, or peeling when the stent is flexed, crimped, expanded, or subjected to intravascular forces. Any of the foregoing results of excessively thick coatings may reduce the antithrombogenic characteristics of the stent. Moreover, the likelihood of pitting is hypothesized to be greater in thick coatings, and pits in a coating may increase the susceptibility to galvanic corrosion of the underlying surface. Because their fabrication requires additional steps, coatings comprising multiple layers may also be more difficult and expensive to manufacture Accordingly, a need exists for a thromboresistant coating that is thin, durable, and biocompatible, and that may be applied in a single coating.

SUMMARY OF THE INVENTION

Coatings are provided herein in which biopolymers may be covalently linked to a substrate. Such biopolymers include those that impart thromboresistance and/or biocompatibility to the substrate, which may be a medical device. Coatings disclosed herein include those that permit coating of a medical device in a single layer, including coatings that permit applying the single layer without a primer. It should be understood that it may be advantageous in some circumstances to apply double layers of the coatings, such as to cover an area of a medical device that is used to hold the device while a first layer is applied. Thus, single, double and multiple layers of coatings are encompassed by the coatings disclosed herein.

The coatings disclosed herein include those that use an adduct of heparin molecules to provide thromboresistance.

The heparin molecules may comprise heparin-tri(dodecyl) methylammonium chloride complex. Uses of the term "heparin" herein should be understood to include heparin, as well as any other heparin complex, including heparin-tri (dodecyl)methylammonium chloride complex.

The coatings described herein further include those that use a silane to covalently link a biopolymer to a substrate. The coatings include those derived from silanes comprising isocyanate functionality.

The disclosed coatings include those that can be applied without a base or primer layer.

Coatings are also included that provide a thin and durable coating wherein the thickness of said coating can be controlled by application of single or multiple layers.

Coatings are provided wherein thromboresistance activity can be modified by choice of appropriate amounts of heparin-TDMAC complex and silane.

Thin, durable coatings are provided having controllable bioactivity.

Single or multi-layer coatings disclosed herein are designed to impart thromboresistance and/or biocompatibility to a medical device. In one embodiment, the coating provides for covalent linking of heparin to the surface of the medical device.

One coating formulation of the present invention initially consists of heparin-TDMAC complex, organic solvent and silane. Wetting agents may be added to this formulation. A silane is chosen that has an organic chain between isocyanate and silane functionalities. The isocyanate functionality reacts with an amino or hydroxyl group on the heparin molecule. After the reaction, the formulation contains covalent adducts of heparin and silane, in addition to organic solvent and other additives. Unreacted silane or heparin-TDMAC complex may be present in the formulation, depending on the relative amounts of the reagents utilized.

Once the coating formulation is applied to a device, the silane end group of the adduct mentioned above adheres to the substrate surface, and a network, or film, containing heparin-TDMAC complexes is created on the surface of a substrate. Heparin molecules in the heparin-TDMAC complex are known to have anticoagulant properties. When exposed to blood, heparin molecules inactivate certain coagulation factors, thus preventing thrombus formation.

The direct adherence of the silane end group to the substrate means that the coating may be applied to a wide range of medical device materials without the use of a base/primer layer. The covalent bond between the surface and the silicon of the silane comprising the heparin-TDMAC complex provides superior durability compared to known coatings.

The coating can be applied by dip coating, spray coating, painting or wiping. Dip coating is a preferred mode.

The coating can be thin and durable. The coating thickness can be controlled in a number of ways, e.g., by the application of single or multiple layers. Since the coating process described herein may be a one-step process, coating thickness is not increased as a result of the need to apply multiple layers, as in certain known coating methods.

The bioeffectiveness of the coatings can be controlled by selecting appropriate amounts of reactants. In particular, the thromboresistance activity of the coating can be controlled by modifying the amount of heparin-TDMAC complex in the coating.

DETAILED DESCRIPTION OF THE INVENTION

Single or multi-layer coatings are provided herein that are designed to impart thromboresistance and/or biocompatibility to a medical device. In an embodiment of the invention, the coating provides for the covalent linking of heparin molecules to a substrate.

A heparin molecule is understood to contain a specific art-recognized pentasaccharide unit that displays antithrombogenic qualities. Covalent linkage of a heparin molecule to a surface is understood to affect at least one, but not all, of the hydroxyl and amino moieties comprised by that molecule; the covalently linked heparin, therefore, presents a thromboresistant surface to the environment surrounding the coated substrate. Different methods and formulations for covalently linking heparin to the surface may affect different sites on the heparin molecules, so that different formulations will provide different levels of anti-thrombogenicity.

One coating formulation of the present invention initially consists of heparin-TDMAC complex, organic solvent and a silane. Other biopolymers may be used in place of or in addition to heparin-TDMAC complex, and such biopolymers may be covalently linked to a substrate according to the present invention. Such biopolymers may be those that provide thromboresistance, or those that have other desired bioactivity.

The silane provided may have functionality capable of reacting with a nucleophilic group, e.g., a hydroxyl or amino group. In particular, the silane may comprise isocyanate, isothiocyanate, ester, anhydride, acyl halide, alkyl halide, epoxide, or aziridine functionality. In certain embodiments described herein, the silane comprises isocyanate functionality.

The silane comprising isocyanate functionality may be linked covalently to any biopolymer that provides antithrombogenicity. The selected biopolymer may be selected from a group of heparin complexes, including heparin-tridodecylmethylammonium chloride, heparin-benzalkonium chloride, heparin-stearalkonium chloride, heparin-poly-N-vinyl-pyrolidone, heparin-lecithin, heparin-didodecyldimethyl ammonium bromide, heparin-pyridinium chloride, and heparin-synthetic glycolipid complexes. The selected biopolymer may also be another biopolymer that has hydroxyl or amine functional groups that can react with the isocyanate functionality of the silane.

The selected biopolymer is preferably capable of dissolving in an organic solvent, as opposed to biopolymers that dissolve only in water. Solubility in organic solvents confers a number of advantages, e.g., elimination of water-mediated decomposition of the isocyanate-containing silane.

In one preferred embodiment, the selected biopolymer is heparin-tri(dodecyl)methylammonium chloride complex.

Wetting agents and other additives may be added to the coatings described herein to improve the adherence to the substrate, to improve the ease of adding the coatings to a substrate, or for other purposes. A variety of organic solvents may be used, including tetrahydrofuran (THF). Additives may include surface active agents, such as Triton.

The selected silanes may have an organic chain between the isocyanate functionality, which covalently links to the heparin molecule, and an end group that is capable of linking to a substrate surface. The end group may link to pendant oxide groups on the substrate surface; in some cases the pendant oxide groups may be obtained by oxidation of the substrate.

The bioactivity, including thromboresistance, of the disclosed coatings may be selectively modified by controlling the amounts of heparin-tridodecylmethylammonium chloride complex, silane comprising isocyanate functionality, and organic solvent, as well as other constituents, to provide the desired thromboresistance. In an embodiment of the coatings, the concentration of the silane in the formulation is between about one-half percent and about four percent. In an embodiment, the concentration of heparin-tridodecylmethylammonium chloride in the formulation is between about one-tenth percent and about four percent. One preferred coating is a solution with a formulation of silane of about five-tenths percent and a formulation of the heparin-tridodecylmethyl-ammonium chloride complex of about two-tenths percent. In one such preferred solution, the organic solvent is tetrahydrofuran.

Heparin molecules, including those in heparin-TDMAC complex are known to have anticoagulant properties. When exposed to blood, structural elements of heparin molecules inactivate certain coagulation factors, thus preventing thrombus formation.

The coatings described herein may be applied in a single layer. The layer can be formed by reacting silane having isocyanate functionality with a heparin in an organic solvent to form a silane-heparin complex, which can be applied directly to a substrate, such as a metal substrate, in a single-layer coating that can be applied without a primer. The single layer can thus be made sufficiently thin to minimize the problems of peeling, cracking, and other problems that characterize some thicker coatings that require multiple layers, primers, or polymeric matrices for binding to the substrate. Thus, the layers may perform better under the mechanical crimping or expansion of a medical device, such as a stent, to which they are applied, and may perform better in the intravascular environment.

The silane end groups of the monomer that yield the coatings react with oxides or hydroxyl groups on the surface of stainless steel. The stainless steel surface may be oxidized or cleaned and pre-treated, such as with sodium hydroxide, to increase the number of appropriate sites for linking the silane end groups.

To improve hydrolytic stability, non-functional silanes can be added to the formulations disclosed herein. Other silanes may be used to link to substrates, such as trihalosilanes, and silanes having methoxy and ethoxy groups. Silanes having triethoxy, trialkoxy, trichloro, and other groups may be provided to yield the covalent linkages present in the coatings disclosed herein. The non-functional silanes may be selected from the group consisting of chain alkyltrialkoxysilanes and phenyltrialkoxysilanes.

In an embodiment, the amount of functional silane is preferably selected to provide substantially complete coverage of the substrate surface, that is, it may be desirable to have the single layer cover all of the surface that would otherwise be exposed to the environment in which the substrate will be placed.

The adherence of the silane end group to the substrate means that the coating may be applied to a wide range of medical device materials without the use of base/primer layer. The covalent bond between the heparin-TDMAC complex and the substrate provides a thin and durable coating. The coating's thickness can be controlled, e.g. by choice of the length of the chain connecting the silane and isocyanate functionalities.

The bioeffectiveness and/or bioactivity of the thromboresistant coating can be controlled by selecting appropriate amounts of reactants. In particular, the thromboresistance activity of the coating can be modified by modifying the amounts of heparin-TDMAC complex and silane in the coating.

Single layers have further advantages in that problems may arise in the extra steps required for the deposition of multiple layers. For example, dust or other particulates may appear between coatings in two-step processes. Also, application of a second layer may tend to reduce reactivity of the first layer in an unpredictable way.

Coatings of the present invention may be applied to medical devices that are placed in the body of a human, or that remain outside the body. Coated medical devices that are placed in the human body may include stents, cathethers, prostheses and other devices. Coated medical devices that remain outside the human body may include tubing for the transport of blood and vessels for the storage of blood. Substrates or medical devices on which the coatings described herein may be applied can include a wide variety of materials, including stainless steel, nitinol, tantalum, glass, ceramics, nickel, titanium, aluminum and other materials suitable for manufacture of a medical device.

The coatings disclosed herein may further include a film-forming agent for the coating. The film-forming agents could slow any leaching of the biopolymer from the coating. The film forming-agent could be added in a second layer, or dissolved simultaneously with the silane and the biopolymer. Appropriate film-forming agents could include cellulose esters, polydialkyl siloxanes, polyurethanes, acrylic polymers or elastomers, as well as biodegradable polymers such as polylactic acid (PLA), polyglycolic acid (PGA), copolymers of PLA and PGA, known as PLGA, poly(e-caprolactone), and the like.

To create coatings of the present invention, the silanes and heparin complex are dissolved in a solvent, which may be an organic solvent. The solutions preferably should be substantially anhydrous, because water tends to react with isocyanate groups of the silane molecule. The water may be added after mixing the silane-isocyanate with heparin. In certain embodiments, the silane and heparin are combined in solution, the resulting solution is aged for about one day, the pH is adjusted with a weak acid, and then water is added to hydrolyze silane. The pH of the solution may be adjusted with aqueous acetic acid. Instead of adding water, it is possible to hydrolyze the silane groups by exposure to moist atmospheric conditions. It is desirable to mix the silane and heparin complex in a manner so as to include a slight excess of heparin molecules, so that all of the isocyanate is reacted, preventing adverse reactions between the isocyanate and any water. Moreover, it is desirable to have a single heparin react with each silane isocyanate functional group, this goal is most easily accomplished by starting with an excess of heparin.

Based on experimental results, it was found that, in certain embodiments, solutions of about two-tenths percent heparin complex and about five-tenths percent silane provided effective coatings. However, coatings in a fairly wide range may be effective. Thus, coatings are likely to have some effectiveness in cases in which heparin complex is present in concentrations ranging from about one-tenth of a percent to about twenty percent. Coatings with heparin in concentrations of less than ten percent may be preferable in some formulations. Coatings with heparin in concentrations of less than five percent may be preferable in other formulations. Coatings may be expected to be effective in formulations in which silane is present in a wider range of concentrations as well, including concentrations ranging from about one-tenth of a percent silane to about twenty percent silane.

The thromboresistant characteristics of heparin coatings can be assessed qualitatively and quantitatively, so that methods can be developed that provide uniform coating with a desired amount of bioactivity. Successfully heparinized surfaces give a purple stain when exposed to toluidine blue. After coating, the surface is exposed to a saline solution for a number of days or weeks, and thromboresistance activity is measured as a function of time. Stents and coupons coated as disclosed herein were shown experimentally to display long-lived thromboresistant properties, bioactivity persisted for periods on the order of months, and it will probably endure much longer.

The heparin activity of a sample may be quantified based on its ability to inactivate thrombin. To quantized heparin activity in experimental assays, heparin may be first mixed with human antithrombin III, which binds to create a complex. The heparin-antithrombin III complex can then be mixed with thrombin to produce a ternary complex comprising heparin, thrombin, and antithrombin. The heparin then departs this complex and is free to react again with available antithrombin and thrombin to create additional thrombin-antithrombin complexes. Thus, heparin acts as a catalyst for the antithrombin-mediated deactivation of thrombin. The reaction of the active thrombin still left in the solution with a substrate produces a proportional amount of p-nitro aniline exhibiting color. Thus, an assay may be conducted for a spectrophotometric analysis of color, to determine the amount of thrombin left in solution. The more thrombin left in solution, the lower the bioactivity of the heparin. A low level of thrombin in solution indicates a high degree of catalysis of the thrombin-antithrombin reaction, which indicates a high level of thromboresistance provided by the heparin. A baseline comparison for the assay is the very slow reaction of thrombin-antithrombin in the absence of heparin. The results of the assay can be quantified using spectrophotometry. The assay mimics the reactions that occur in the human bloodstream, where thrombin and antithrombin circulate at all times. The reaction between antithrombin and thrombin in the body, which is catalyzed by the heparin of the coatings of the present invention, helps suppress the coagulation that results from thrombogenesis on a medical device.

Various methods of making coatings of the present invention are possible, and examples of such methods and certain resulting coatings are as follows. Such methods and coatings are disclosed by way of example, and are not intended to be limiting, as other examples may be readily envisioned by one of ordinary skill in the art. The following examples include methods of providing coatings of the present invention in a single layer without the need for a primer layer, as well as methods of controlling the bioactivity of the resulting coating. In some instances, experimental results are provided showing sustained bioactivity for the particular coating.

Coatings can be applied in a wide variety of conventional ways, including painting, spraying, dipping, vapor deposition, epitaxial growth and other methods known to those of ordinary skill in the art.

To test coatings disclosed herein, infrared scans were performed to demonstrate changes in the isocyanate functionality, through observation of the isocyanate peak (NCO, 2260 or 2270 cm$^{-1}$) over time. Isocyanatosilane was formulated with different components, including heparin-tridodecylmethylammonium chloride complex (Heparin-TDMAC complex), tetrahydrofuran ("THF") and Triton (an optional, surface active agent) in solution to determine whether the intensity of the isocyanate peak changed over time. Table I shows the observation of the isocyanate functionality for different solution constituents.

TABLE 1

| Solution | Observation |
| --- | --- |
| 1) Silane - THF | No change in peak with time |
| 2) Silane - THF - TDMAC | No change in peak with time |
| 3) Silane - THF - Triton | No change in peak with time |
| 4) Silane - THF - Heparin-TDMAC complex | Peak disappears with time depending on the concentration of silane and heparin-TDMAC complex |

The observation that the isocyanate peak disappears with time in the solution that includes silane, THF and Heparin-TDMAC complex suggests that a reaction occurs between functional groups on heparin and the isocyanate group of silane.

In embodiments of the present invention, the coating formulation contains the following constituents, which may vary in concentrations in different embodiments: Heparin-TDMAC complex, an organic solvent, such as THF, a silane, such as 3-isocyanatopropyl triethoxysilane (OCN—(CH$_2$)$_3$—Si(OEt)$_3$), and Triton (x-100). In a first embodiment, a solution of these constituents was mixed and allowed to sit in order to permit a reaction to occur. Allowing the solution to sit for one day allowed the reaction to occur, but shorter reaction times may well be effective. Before coating the substrate with the solution, the pH was adjusted. Solutions of the above constituents were adjusted to a pH between 4.5 and 5.5 using a solution of acetic acid and water. After adjusting pH, it is desirable to wait for a period of time, such as fifteen minutes, before applying the coating. Once the coating was applied, it was dried in air and cured in an oven. In particular, coatings of the above constituents were dried in air for about twenty minutes and then cured in an oven at 85 degrees Celsius for about one hour.

Coatings, derived from the above-described solutions, on coupons and stents were tested in various ways. First, as a qualitative test, coated coupons and stents were dipped in toluidine blue solution and then were screened for the presence of a purple stain. As mentioned above, the presence of a purple stain in this assay indicates the presence of heparin in the sample being assayed. Additionally, the intensity of the purple stain observed in this assay is proportional to the amount of heparin in the sample. Therefore, a comparison of the intensities of the purple stains produced in this assay by a set of samples allows an assignment of the relative amounts of heparin comprised by the coatings of those samples.

As a quantitative test for heparin activity a heparin activity assay was conducted according to a conventional thrombin inhibition assay technique. The heparin assay permitted determination of the ability of the heparin coating to deactivate thrombin and thus to provide thromboresistance. The purpose of the protocol was to assay for heparin activity based on thrombin inhibition. A number of different reactions are understood to take place in order to determine heparin activity. In the first reaction:

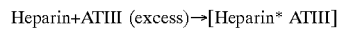

Heparin+ATIII (excess)→[Heparin* ATIII]

Heparin reacts with Human Antithrombin III ("ATIII") to yield a Heparin-Antithrombin III complex. In the second reaction

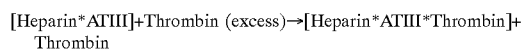

[Heparin*ATIII]+Thrombin (excess)→[Heparin*ATIII*Thrombin]+ Thrombin the Heparin-Antithrombin complex reacts with Thrombin to yield a Heparin-Antithrombin-Thrombin complex. In the third reaction:

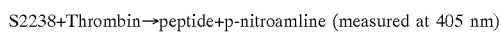

S2238+Thrombin→peptide+p-nitroamline (measured at 405 nm)

the amount of the thrombin was measured. As a result, the size of the p-nitroaniline peak measured at 405 nm is inversely proportional to the amount of heparin present.

EXAMPLES

The invention now being generally described, it will be more readily understood by reference to the following examples which are included merely for purposes of illustration of certain aspects and embodiments of the present invention, and are not intended to limit the invention.

General Procedures

In the following examples, heparin activity on coated coupons or stents was measured after exposing the coated object to a continuous flow of saline at 37° C. for a selected time period. Stainless steel coupons and stents were cleaned before coating. The coupons or stents were cleaned with several organic solvents, such as hexane and isopropanol, followed by rinsing with distilled water. The cleaning procedure was carried out in an ultrasonic bath for fifteen minutes. After this procedure, the coupons or stents were placed in sodium hydroxide solution (1.0 N) for fifteen minutes and then washed thoroughly with distilled water. Samples were air dried before coating.

It should be noted that thrombin inhibition assay techniques are notoriously subject to significant sample error; accordingly, it is not unusual to obtain variable experimental results for a given sample. The examples below identify results for multiple samples under a variety of conditions and thus indicate in the aggregate that the coatings described herein are likely to provide therapeutic levels of thromboresistance. However, results from any single formulation were found to vary somewhat depending on particular sample conditions. In cases where more than one set of data is provided for a given sample, the individual data sets reflect measurements taken at distinct positions on that sample, the data sets in these cases, therefore, do not necessarily reflect a lack of precision in the measurements.

Example 1

Stainless steel coupons were coated with a formulation of 1% heparin-TDMAC complex, 2% silane and 97% THF. The coupons were dipped once in the formulation, with a dwell time of five seconds at a coating speed of 10 in/min, to give a single layer of coating. Results are set forth in Table 2.

TABLE 2

| | Activity, mU/cm$^2$ | |
| --- | --- | --- |
| Sample | Unwashed | 7 days wash |
| 97-080-90C | <10 | <10 |
| 97-080-90C | <15 | <10 |
| 97-080-90D | <15 | <5 |
| 97-080-90D | <15 | <5 |

The coating showed toluidine blue stain before and after washing with water. The coating showed heparin activity after one week of exposure to saline.

Example 2

Stainless steel coupons were dipped once, at coating speeds of 10 in/min and 42 in/min and for a dwell time of five seconds, and resulting in singe layer coatings of different thickness, in the following formulations: 1) 7% heparin-TDMAC complex, 2% silane and 91% THF and a small amount of Triton; and 2) 2% heparin-TDMAC complex, 2% silane and 96% THF and a small amount of Triton. Sample pieces were cut from coupons and were either washed or not washed before being measured under the indicated conditions after the indicated amounts of time. Results are set forth in Table 3:

TABLE 3

| | Activity, mU/cm$^2$ | | | | |
| --- | --- | --- | --- | --- | --- |
| Sample | 1 day unwashed | 2 days unwashed | 1 day wash | 2 days wash | 7 days wash |
| 97-100-9A | <50 | <75 | <15 | <25 | <25 |
| 97-100-9A | <50 | <75 | <15 | <25 | <25 |
| 97-100-9B | <50 | <75 | <25 | <50 | <50 |
| 97-100-9B | <75 | <75 | <15 | <50 | <10 |

A toluidine blue stain was present before and after washing, and the coupons showed heparin activity after seven days of washing. Combined with Example 1, the results showed that heparin activity can be varied using different coating formulations and coating processes.

Example 3

Stainless steel coupons were dipped once, at speeds of 10 in/min and 42 in/min, and for dwell times of five seconds, two minutes and fifteen minutes, and resulting in coatings of different thickness, in the following formulations 1) 7% heparin-TDMAC complex, 2% silane and 91% THF and a small amount of Triton; and 2) 2% heparin-TDMAC complex, 2% silane and 96% THF and a small amount of Triton. Results are shown in Table 4.

TABLE 4

| | Activity, mU/cm$^2$ | | |
| --- | --- | --- | --- |
| Sample | 1 day unwashed | 1 day wash | 7 days wash |
| 97-100-15A | <150 | <10 | <5 |
| 97-100-15A | <100 | <10 | <10 |
| 97-100-15B | <50 | <10 | <25 |
| 97-100-15B | <25 | <1 | <25 |
| 97-100-15C | <75 | <25 | |
| 97-100-15C | <100 | <50 | |
| 97-100-15D | <150 | <50 | |
| 97-100-15D | <150 | <50 | |
| 97-100-15E | <150 | <10 | <10 |
| 97-100-15E | <150 | <25 | <25 |
| 97-100-15F | <150 | <10 | <25 |
| 97-100-15F | <200 | <25 | <25 |
| 97-100-15G | <150 | <25 | |
| 97-100-15G | <150 | <25 | |
| 97-100-15H | <150 | <50 | |
| 97-100-15H | <150 | <50 | |
| 97-100-15I | <200 | <100 | <50 |
| 97-100-15I | <200 | <75 | <75 |
| 97-100-15J | <200 | <100 | |
| 97-100-15J | <250 | <100 | |

Seven day results were for certain pieces measured at the one day point and then placed back into a flusher for additional days of washing. Toluidine blue stains were present before and after wash, with shades differing with thickness. Heparin activity was present after seven days of washing. In combination with Examples 1 and 2, this example demonstrated that heparin activity can be varied using different coating formulation and coating processes

Example 4

Stainless steel coupons were dipped once, at speeds of 10 in/min for dwell times of one-half, one, two, five, ten and fifteen minutes, in the following formulation: 2% heparin-TDMAC complex, 2% silane, 96% TBF and a small amount of Triton. Certain coupons were dipped into toluidine blue solution and rubbed under water. The coupons were then redipped in toluidine blue and checked for the presence of a stain. Results are shown in Table 5.

TABLE 5

| Sample | Appearance | Toluidine blue stain before rub test | Toluidine blue stain after rub test |
| --- | --- | --- | --- |
| 97-100-30A | Good coating, thin | Uniform, light | Uniform, light |
| 97-100-30B | Good coating, thin | Uniform, light | Uniform, light |
| 97-100-30C | Good coating, thin | Uniform, light | Uniform, light |
| 97-100-30D | Good coating, thin | Uniform, light | Uniform, light |
| 97-100-30E | Good coating, thin | Dark gritty stain | Uniform, light, some peeling |

A qualitative assessment of the effect of different solvents on coating was also performed, by dipping a coated sample in solvent for 60 seconds and then washing it with water and staining it with toluidine blue. Results are shown in Table 6.

TABLE 6

| | Solvent | | | | |
| --- | --- | --- | --- | --- | --- |
| Sample | IPA | Toluene | Hot water (high pressure flow) | Hot water (high pressure flow) | Acetone |
| 97-100-30G | Good purple stain | No stain | Light stain | Light stain | Good stain |

Heparin activity is displayed in Table 7.

TABLE 7

| | Activity, mU/cm$^2$ | |
| --- | --- | --- |
| Sample | 1 day unwashed | 1 day wash |
| 97-100-30A | <150 | <25 |
| 97-100-30A | <150 | <25 |
| 97-100-30B | <75 | — |
| 97-100-30B | <75 | — |
| 97-100-30C | <50 | — |
| 97-100-30C | <50 | — |
| 97-100-30D | <50 | — |
| 97-100-30D | <50 | — |
| 97-100-30E | <10 | — |
| 97-100-30E | <25 | — |
| 97-100-30F | <10 | — |
| 97-100-30F | <25 | — |
| 97-100-30G | <25 | <25 |
| 97-100-30G | <25 | <25 |

This example indicated that coating thickness may be dependent on dwell time, that rubbing does not remove the coating as indicated by stains after rubbing, that washing with various solvents has a different effect on coating durability, and that heparin activity was present after washing. The example provided further evidence that heparin activity can be varied using different coating processes.

Example 5

Stainless steel coupons were dipped once, at speeds of 10 in/min and for dwell times of two and fifteen minutes, in the following formulations: 1) 2% heparin-TDNAC complex, 4% silane and 94% THF and a small amount of Triton; 2) 2% heparin-TDMAC complex, 8% silane and 90% THF and a small amount of Triton; 3) 4% heparin-TDMAC complex, 4% silane and 92% THF and a small amount of Triton; and 4) diluted 4% heparin-TDMAC complex, 4% silane and 92% THF and a small amount of Triton.

Coated coupons were dipped in toluidine blue solution and rubbed with fingers under water, then redipped in toluidine blue and checked for stains. Results are displayed in Table 8.

TABLE 8

| Sample | Apearance | Toluidine blue stain before rub test | Toluidine blue stain after rub test |
| --- | --- | --- | --- |
| 97-100-36A (2 min) | Good coating | Uniform stain | Uniform |
| 97-100-36A (15 min) | Good coating | Uniform stain | Uniform |
| 97-100-36B (2 min) | Good coating | Uniform stain | Uniform |
| 97-100-36B (15 min) | Good coating | Uniform stain | Uniform |
| 97-100-36C (15 min) | Good coating | Very thick, gritty | Uniform, some peeling |
| 97-100-36C (15 min) | Good coating | Very thick, gritty | Uniform, some peeling |
| 97-100-36D (2 min) | Good coating | Uniform stain | Uniform |
| 97-100-36D (15 min) | Good coating | Uniform stain | Uniform, some peeling |

Heparin activity for this example is displayed in Table 9.

TABLE 9

| | Coating | Activity, mU/cm$^2$ | | | | |
| --- | --- | --- | --- | --- | --- | --- |
| Sample | (%/% heptdmac silane) | 1 day un-washed | 30 days un-washed | 1 day wash | 30 days wash | 87 days wash |
| 97-100-36A (2 min dwell) | 2.0/4.0 | <150, <125 | <50 | <25, <25 | <5 | <1, <1 |
| 97-100-36B (2 min) | 4.0/8.0 | <25, <25 | <25 | <25, <25 | <5 | <1, <1 |
| 97-100-36C (2 min) | 4.0/4.0 | <175, <150 | <150 | <50, <25 | <5 | <1, <1 |
| 97-100-36C (2 min) | Diluted, 4.0/4.0 | <50, <100 | <150 | <25, <25 | <5 | 0, <1 |

This example demonstrated that for thin coatings thickness is not strongly dependent on dwell time. Also, rubbing does not remove the coating, as indicated by stains after rubbing. Long term durability of the coating is evident from heparin activity results. Again, heparin activity can be varied using different coating formulation and processes.

Example 6

Stainless steel coupons were dipped once, at speeds of 10 in/min and for a dwell time of two minutes, in the following formulation: 2% heparin-TDMAC complex, 2% silane and 96% THF and a small amount of Triton. The coupons were then either left unsterilized, or sterilized with ethylene oxide or gamma radiation.

Results for non-sterile coupons are in Table 10.

TABLE 10

| Sample | Coating (%/% heptdmac salane) | Dip | Activity, mU/cm² | | | |
|---|---|---|---|---|---|---|
| | | | Un-washed, 7 days | Un-washed, 28 days | 7 days wash | 28 days wash |
| 97-100-66A | 2.0/2.0 | Single | <125, <100 | >10, >12 | <10, <10 | <2, <1 |
| 97-100-66E | 2.0/2.0 | Single | <100, <125 | >10, >16 | <10, <10 | <1, 0 |

Results for ethylene oxide sterile coupons are in Table 11.

TABLE 11

| Sample | Coating (%/% heptdmac salane) | Dip | Activity, mU/cm² | | | |
|---|---|---|---|---|---|---|
| | | | 1 day, unwashed | 14 days, unwashed | 1 day | 14 days |
| 97-100-66A | 2.0/2.0 | Single | >12 | >16, >16 | <15 | <2, <2 |
| 97-100-66E | 2.0/2.0 | Single | >12 | >16, >16 | <10 | <2, <2 |

Results for gamma radiation sterilized coupons are in Table 12.

TABLE 12

| Sample | Coating (%/% heptdmac salane) | Dip | Activity, mU/cm² | | | | | |
|---|---|---|---|---|---|---|---|---|
| | | | 1 day unwashed | 14 days unwashed | 20 days unwashed | 1 day wash | 14 days wash | 20 days wash |
| 97-100-66A | 2.0/2.0 | Single | <200, <200 | >16 | >16 | <20, <20 | <1, <1 | <1, <2 |
| 97-100-66E | 2.0/2.0 | Single | <200, <200 | >16 | >16 | 0.0 | <2, <2 | <2, <2 |

The resulting coatings were thin, with long term durability as evident by heparin activity results. Sterilization did not appear to affect coating properties, regardless of the sterilization mode.

Example 7

Stainless steel coupons were dipped once, dipped twice, or dipped, washed, and then dipped again, at coating speeds of 10 in/min and for dwell times of two minutes, in the following formulations: 1) 0.5% heparin-TDMAC complex, 0.5% silane, 99% THF and a small amount of Triton; 2) 0.5% heparin-TDMAC complex, 2.0% silane, 97.5% THF and a small amount of Triton; 3) 2.0% heparin-TDMAC complex, 0.5% silane, 97.5% THF and a small amount of Triton; and 4) 2.0% heparin-TDMAC complex, 2.0% silane, 96% TET and a small amount of Triton.

Heparin activity is shown in Table 13.

TABLE 13

| Sample | Coating (%/% heptdmac salane) | Dip | Activity, mU/cm² | | | | | |
|---|---|---|---|---|---|---|---|---|
| | | | 12 days unwashed | 18 days unwashed | 12 day wash | 18 day wash | 24 day wash | 72 day wash |
| 97-100-69A | 0.5/0.5 | Single | >10 | <175 | 0 | <5 | — | 0 |

TABLE 13-continued

| Sample | Coating (%/%) heptdmac salane | Dip | Activity, mU/cm² | | | | | |
|---|---|---|---|---|---|---|---|---|
| | | | 12 days unwashed | 18 days unwashed | 12 day wash | 18 day wash | 24 day wash | 72 day wash |
| 97-100-69B | 0.5/0.5 | Double | >10 | <150 | <2 | <2 | — | <1 |
| 97-100-69C | 0.5/0.5 | Dip/wash/Dip | >10 | <125 | <2 | <2 | <2 | <1 |
| 97-100-69D | 0.5/2.0 | Single | >10 | <75 | <1 | <5 | — | <1 |
| 97-100-69E | 0.5/2.0 | Double | <5 | <5 | <1 | <5 | — | <1 |
| 97-100-69F | 0.5/2.0 | Dip/wash/Dip | <2 | <5 | <2 | <5 | <2 | <1 |
| 97-100-69G | 2.0/0.5 | Single | — | <15 | — | <5 | — | <1, <1 |
| 97-100-69H | 2.0/0.5 | Double | — | <5 | — | <5 | — | <1, <1 |
| 97-100-69I | 2.0/0.5 | Dip/wash/Dip | — | <2 | — | <5 | <2, <2 | 0, <1 |
| 97-100-69J | 2.0/2.0 | Single | — | <150 | — | <5 | — | <1, <1 |
| 97-100-69K | 2.0/2.0 | Double | — | <200 | — | <5 | — | <1, <1 |
| 97-100-69K | 2.0/2.0 | Dip/wash/Dip | — | <250 | — | <5 | <3, <2 | <1, <1 |

The resulting thin coatings demonstrated heparin activity, including light stains before and after rubbing. The long term durability of the coatings were evident through heparin activity results. Coating properties were variable according to different coating methods.

Example 8

Stainless steel coupons were dipped twice, or were dipped, washed, and dipped again, at speeds of 10 in/min and for dwell times of two minutes, in the following formulations: 1) 0.5% heparin-TDMAC complex, 0.5% silane, 99% THF; and 2) 0.5% heparin-TDMAC complex, 2.0% silane, 97.5% THF. The pH of the coatings was adjusted using acetic acid.

Heparin activity is shown in Table 14.

TABLE 14

| Sample | Coating (%/% heptdmac salane) | Dip | Activity, mU/cm² | | |
|---|---|---|---|---|---|
| | | | 1 day unwashed | 1 day | 43 days |
| 97-100-93A | 0.5/0.5 | Double | <75 | <2 | <2, <1 |
| 97-100-93B | 0.5/0.5 | Dip/wash/dip | <50 | <3 | <1, <1 |
| 97-100-93C | 0.5/2.0 | Double | <50 | <2 | <2, <2 |
| 97-100-93D | 0.5/2.0 | Dip/wash/dip | <1 | <1 | <2, <2 |

The resulting thin coatings demonstrated heparin activity, including light stains before and after rubbing. The long term durability of the coatings was evident through heparin activity results. Coating properties were variable according to different coating methods.

Example 9

Stainless steel coupons and stainless steel stents were dipped twice, or were dipped, washed with saline and distilled water, and dipped again, at coating speeds of 10 in/min and for dwell times of two minutes Coating pH was adjusted using hydrochloric acid. Coating's derived from the following formulations were prepared: 1) 0.5% heparin- TDMAC complex, 0.5% silane, 99% THF; and 2) 0.5% heparin-TDMAC complex, 2.0% silane, 97.5% THF.

Heparin activity is shown in Table 15.

TABLE 15

| | Coating (%/%) | | Activity, mU/cm$^2$ | | | | | |
|---|---|---|---|---|---|---|---|---|
| Sample | heptdmac salane | Dip | 1 day unwashed | 11 days unwashed | 1 day wash | 11 days wash | 25 days wash | 43 days wash |
| 97-100-92A | 0.5/0.5 | Double | <25 | <25, <25 | <2 | <1, <1 | <1, <1, <5, <2, <2, <2 | — |
| 97-100-92B | 0.5/0.5 | Dip/wash/Dip | <25 | <25, <25 | <2 | >1, <1 | <2, <2, <2, <2, <1, <2 | — |
| 97-100-92C | 0.5/2.0 | Double | <10 | | <5 | — | <5, <2 | <1, <2 |
| 97-100-92D | 0.5/2.0 | Dip/wash/Dip | <25 | | <2 | — | <2, <2 | <1, <1 |

Persistence of heparin activity after an increasing number of days suggests that most unattached heparin washes away immediately, but that attached heparin does not easily wash away even after prolonged exposure.

Activity on stents is disclosed in Table 16.

TABLE 16

| | Coating (%/% | | Activity, mU/cm$^2$ | |
|---|---|---|---|---|
| Sample | heptdmac salane) | Dip | 1 day unwashed | 1 day |
| 97-100-92C | 0.5/0.5 | Dip/wash/Dip | <125 | <50 |
| 97-100-92F | 0.5/2.0 | Dip/wash/Dip | <50 | <50 |

The resulting thin coatings showed light stains before and after rubbing. The coatings were durable as evident from heparin activity results. Coating properties were variable depending on different coating methods.

Example 10

Stainless steel coupons and stainless steel stents were dipped, washed with IPA and dipped again, at coating speeds of 10 in/min and for a dwell time of two minutes, in the following formulations: 1) 0.1% heparin-TDMAC complex, 0.5% silane, 99.4% THF, and 2) 0.2% heparin-TDMAC complex, 0.5% silane, 99.3% THF.

Heparin activity on coupons is shown in Table 17.

TABLE 17

| | Coating | | Activity, mU/cm$^2$ | | |
|---|---|---|---|---|---|
| Sample | (%/% heptdmac salane) | Dip | 2 days unwashed | 2 days wash | 34 days wash |
| 97-101-25A red | 0.1/0.5 | Double | <25 | <1 | <2 |
| 97-101-25A red | 0.1/0.5 | Double | <25 | <1 | <2 |
| 97-101-25B green | 0.1/0.5 | Dip/wash/dip | <75 | 0 | <2 |
| 97-101-25B green | 0.1/0.5 | Dip/wash/dip | <50 | 0 | <22 |
| 97-101-25C yellow | 0.1/0.5 | Double | <25 | <1 | <2 |
| 97-101-25C yellow | 0.1/0.5 | Double | <25 | <1 | <2 |
| 97-101-25D brown | 0.1/0.5 | Dip/wash/dip | <75 | 0 | <2 |
| 97-101-25D brown | 0.1/0.5 | Dip/wash/dip | <50 | 0 | <22 |

Heparin activity on stents is shown n in Table 18

TABLE 18

| Sample | Coating (%/% heptdmac salane) | Dip | Activity, mU/cm² | | |
|---|---|---|---|---|---|
| | | | 2 days unwashed | 2 days wash | 16 days wash |
| 97-101-25A red | 0.1/0.5 | Double | <25 | <1 | <2 |
| 97-101-25A red | 0.1/0.5 | Double | <25 | <1 | <2 |
| 97-101-25B green | 0.1/0.5 | Dip/wash/dip | <75 | 0 | <2 |
| 97-101-25B green | 0.1/0.5 | Dip/wash/dip | <50 | 0 | <2 |
| 97-101-25C yellow | 0.2/0.5 | Double | <50 | <1 | <5 |
| 97-101-25C yellow | 0.2/0.5 | Double | <25 | <1 | <5 |
| 97-101-25D brown | 0.2/0.5 | Dip/wash/dip | <50 | <1 | <2 |
| 97-101-25D brown | 0.2/0.5 | Dip/wash/dip | <25 | <1 | <22 |

The resulting thin coatings showed light stains before and after rubbing. The coatings were durable as evident from heparin activity results. Coating properties were variable depending on different coating methods.

Example 11

Stainless steel stents were dipped once, at coating speeds of 10 in/min and for dwell times of five seconds and two minutes, in the following formulations: 1) 4.0% heparin-TDMAC complex, 8.0% silane, 88% THF, small amount of Triton, 2) 4.0% heparin-TDMAC complex, 4.0% silane, 92% TEF, small amount of Triton, and 3) 2.0% heparin-TDMAC complex, 2.0% silane, 96% THF, small amount of Triton.

Heparin activity is shown in Table 19.

TABLE 19

| Sample | Coating (%/% heptdmac salane) | Dip | Activity, mU/cm² | |
|---|---|---|---|---|
| | | | unwashed | 3/4 days |
| 97-100-50A | 4/8 | Single | <175 | <50 |
| 97-101-50B | 4/4 | Single | <150 | <125 |
| 97-100-54B | 2/2 | Single | <225 | <25 (4 days) |

Again, coating properties varied using different coating methods.

Example 12

Stainless steel stents were dipped twice, at coating speeds of 10 in/min and at a dwell time of two minutes, in the following formulations: 1) 0.2% heparin-TDMAC complex, 0.5% silane; 2) 0.5% heparin-TDMAC complex, 0.5% silane; 3) 0.5% heparin-TDMAC complex, 1.0% silane; 4) 1.0% heparin-TDMAC complex, 1.0% silane; and 5) 1.0% heparin-TDMAC complex, 2.0% silane. Stents were either left unsterilized or were sterilized with gamma radiation.

Table 20 shows results for non-sterile stents.

TABLE 20

| Sample | Coating (%/% heptdmac salane) | Dip | Activity, mU/cm² | |
|---|---|---|---|---|
| | | | 4 days unwashed | 4 days |
| 97-101-86A | 0.2/0.5 | Double | <100 | <1 |
| 97-101-86A | 0.2/0.5 | Double | <125 | <1 |
| 97-101-86B | 1.0/2.0 | Double | <200 | <10 |
| 97-101-86B | 1.0/2.0 | Double | <225 | <5 |

TABLE 20-continued

| Sample | Coating (%/% heptdmac salane) | Dip | Activity, mU/cm² | |
|---|---|---|---|---|
| | | | 4 days unwashed | 4 days |
| 97-101-86C | 1.0/1.0 | Double | <225 | <5 |
| 97-101-86C | 1.0/1.0 | Double | <225 | <5 |
| 97-101-86D | 0.5/1.0 | Double | <200 | <5 |
| 97-101-86D | 0.5/1.0 | Double | <225 | <5 |
| 97-101-86E | 0.5/0.5 | Double | <225 | <5 |
| 97-101-86E | 0.5/0.5 | Double | <200 | <5 |
| 97-101-86F | 0.5/1.0 Sutton | Double | <125 | <1 |
| 97-101-86F | 0.5/1.0 Sutton | Double | <125 | <5 |

Table 21 shows activity for sterile stents.

TABLE 21

| Sample | Coating (%/% heptdmac salane) | Dip | Activity, mU/cm² | |
|---|---|---|---|---|
| | | | 4 days unwashed | 4 days |
| 97-101-86A | 0.2/0.5 | Double | <200 | <1 |
| 97-101-86A | 0.2/0.5 | Double | >200 | <5 |
| 97-101-86B | 1.0/2.0 | Double | >200 | <10 |
| 97-101-86B | 1.0/2.0 | Double | >200 | <5 |
| 97-101-86C | 1.0/1.0 | Double | >200 | <10 |
| 97-101-86C | 1.0/1.0 | Double | >200 | <10 |
| 97-101-86D | 0.5/1.0 | Double | >200 | <5 |
| 97-101-86D | 0.5/1.0 | Double | >200 | <5 |
| 97-101-86E | 0.5/0.5 | Double | >200 | <5 |
| 97-101-86E | 0.5/0.5 | Double | >200 | <5 |
| 97-101-86F | 0.5/1.0 Sutton | Double | >200 | <5 |
| 97-101-86F | 0.5/1.0 Sutton | Double | >200 | <5 |

Sterilization showed no effect on coating properties. The coatings were durable on stents, as evident by heparin activity after several days of washing.

Example 13

Several coupons and stents were coated with 0.2% heparin-TDMAC complex, 0.5% silane and 99.3% THF. These pieces were sterilized by gamma radiation and sent to NAMSA for biocompatibility testing. Three tests, Hemolysis, Cytotoxicity and Thromboresistance, were conducted. The coating passed all three tests.

In addition to the foregoing examples, various other methods and coatings may be envisioned in the spirit of the present disclosure. For example, heparin might be covalently linked to a substrate with a silane identified as capable of being soaked into a stainless steel surface. The silane compound could have amino or epoxy terminal groups. The silane could thus be used to link heparin molecules to the substrate in a manner similar to the silane of isocyanate functionality disclosed herein. Heparin could then be prepared with an aldehyde positive group that mixed with an $NH_2$-group to provide an end linkable to heparin without affecting its activity. The procedure to make degraded heparin is well known to those of ordinary skill in the art A coating system may also be provided in which heparin can be covalently linked or can be incorporated into a matrix to obtain variable rate of elution. A silicon fluid, such as Dow Corning MDX 4-4159 is used, with the active silicon being an amino functional polydimethyl siloxane copolymer. The coating may be used to coat stainless steel guide wires. This working can be utilized for heparin covalent-bonding as described below.

First, a solution of heparin (deaminated) in water or other solvent may be provided. A wire coated with a silicon fluid in a solvent may be placed in the solution for some time, for example two hours. The heparin has an aldehyde group that can link to the amino functionality in the silicon copolymer. Other amino functionalized silicon polymers, or copolymers, can be used to achieve covalent bonding of heparin to the substrate.

Equivalents

While the invention has been disclosed in connection with the preferred embodiments shown and described in detail, various modifications and improvements thereon will become readily apparent to those skilled in the art. Accordingly, the spirit and scope of the present invention is to be limited only by the following claims.

We claim:

1. A coating, comprising the product of the reaction of:
   a silane having at least one functional group selected from the group consisting of an isocyanate, an isothiocyanate, an ester, an anhydride, an acyl halide, an alkyl halide, an epoxide and an aziridine; and
   a biopolymer,
   wherein said product is directly coated onto a surface of a medical device by covalent attachment of a silicon atom to said medical device.

2. The coating of claim 1, wherein said functional group is an isocyanate.

3. The coating of claim 2, wherein said biopolymer is heparin-tridodecylmethylammonium chloride.

4. The coating of claim 1, wherein said biopolymer is a complex selected from the group consisting of heparin-tridodecylmethylammonium chloride, heparin-benzalkonium chloride, heparin-stearalkoniun chloride, heparin-poly-N-vinyl-pyrrolidone, heparin-lecithin, heparin-didodecyldimethylammonium bromide, heparin-pyridinium chloride, and heparin-synthetic glycolipid complex.

5. The coating of claim 1, wherein said biopolymer has hydroxyl or amine functional groups.

6. The coating of claim 1, wherein said biopolymer comprises heparin.

7. The coating of claim 5, wherein said biopolymer is provided in a form capable of dissolving in an organic solvent.

8. The coating of claim 1, wherein the biopolymer provides thromboresistance.

9. The coating of claim 1, wherein said biopolymer is heparin-tridodecylmethylammonium chloride.

10. The coating of claim 1, further comprising at least one additive selected from the group consisting of wetting agents, surface active agents and film forming agents.

11. The coating of claim 1, wherein the silane has an organic chain between isocyanate and silane functional groups.

12. A coating, consisting essentially of the product of the reaction of:
    a silane having at least one functional group selected from the group consisting of an isocyanate, an isothiocyanate, an ester, an anhydride, an acyl halide, an alkyl halide, an epoxide and an aziridine; and
    a biopolymer,
    wherein said product is directly bonded to a surface of a medical device.

13. The coating of claim 12, wherein said functional group is an isocyanate.

14. The coating of claim 13, wherein said biopolymer is heparin-tridodecylmethylammonium chloride.

15. The coating of claim 12, wherein said biopolymer is a complex selected from the group consisting of heparin-tridodecylmethylammonium chloride, heparin-benzalkonium chloride, heparin-stearalkonium chloride, heparin-poly-N-vinyl-pyrrolidone heparin-lecithin, heparin-didodecyldimethylammonium bromide, heparin-pyridinium chloride, and heparin-synthetic glycolipid complex.

16. The coating of claim 12, wherein said biopolymer has hydroxyl or amine functional groups.

17. The coating of claim 12, wherein said biopolymer comprises heparin.

18. The coating of claim 12, wherein said biopolymer is provided in a form capable of dissolving in an organic solvent.

19. The coating of claim 12, wherein the biopolymer provides thromboresistance.

20. The coating of claim 12, wherein said biopolymer is heparin-tridodecylmethylammonium chloride.

21. The coating of claim 12, further comprising at least one additive selected from the group consisting of wetting agents, surface active agents and film forming agents.

22. The coating of claim 12, wherein said silane has an organic chain between isocyanate and silane functional groups.

23. The coating of claim 1, wherein said silane and said biopolymer are reacted in a common solvent.

24. The coating of claim 23, wherein said solvent is an anhydrous organic solvent.

25. The coating of claim 24, wherein said solvent is tetrahydrofuran.

26. The coating of claim 12, wherein said silane and said biopolymer are reacted in a common solvent.

27. The coating of claim 26, wherein said solvent is an anhydrous organic solvent.

28. The coating of claim 27, wherein said solvent is tetrahydrofuran.

29. The coating of claim 23, wherein said functional group is an isothiocyanate, said biopolymer is heparin-tridodecylmethylammonium chloride, and said organic solvent is tetrahydrofuran.

30. The coating of claim 26, wherein said functional group is an isothiocyanate, said biopolymer is heparin-tridodecylmethylammonium chloride, and said organic solvent is tetrahydrofuran.

* * * * *